US010426362B2

(12) United States Patent
Melosh et al.

(10) Patent No.: US 10,426,362 B2
(45) Date of Patent: Oct. 1, 2019

(54) DEEP-BRAIN PROBE AND METHOD FOR RECORDING AND STIMULATING BRAIN ACTIVITY

(71) Applicant: The Board of Trustees of the Leland Stanford Junior University, Palo Alto, CA (US)

(72) Inventors: Nicholas Alexander Melosh, Menlo Park, CA (US); Matt R. Angle, Stanford, CA (US); Jun Ding, Palo Alto, CA (US); Andreas Schaefer, London (GB); Mina-elraheb S. Hanna, Stanford, CA (US)

(73) Assignees: The Board of Trustees of the Leland Stanford Junior University, Stanford, CA (US); THE FRANCIS CRICK INSTITUTE, London (GB)

( * ) Notice: Subject to any disclaimer, the term of this patent is extended or adjusted under 35 U.S.C. 154(b) by 759 days.

(21) Appl. No.: 14/937,740

(22) Filed: Nov. 10, 2015

(65) Prior Publication Data

US 2016/0128588 A1 May 12, 2016

Related U.S. Application Data

(60) Provisional application No. 62/077,552, filed on Nov. 10, 2014.

(51) Int. Cl.
*A61B 5/04* (2006.01)
*A61B 5/00* (2006.01)
(Continued)

(52) U.S. Cl.
CPC ........ *A61B 5/04001* (2013.01); *A61B 5/0478* (2013.01); *A61B 5/6868* (2013.01);
(Continued)

(58) Field of Classification Search
CPC ... A61B 5/0476; A61B 5/6846; A61B 5/6847; A61B 5/6848; A61B 2562/0209; A61N 1/0534; A61N 1/36067
See application file for complete search history.

(56) References Cited

U.S. PATENT DOCUMENTS 6,647,297 B2 11/2003 Scribner
8,010,208 B2 * 8/2011 Nimer ..................... A61N 1/05
607/115
(Continued)

OTHER PUBLICATIONS

Tao et al., "Investigation of Process Parameters and Characterization of Nanowire Anisotropic Conductive Film for Interconnection Applications", "Transactions on Components Packaging and Manufacturing Technology", Mar. 2014, pp. 538-547, vol. 4, No. 3, Publisher: IEEE; doi: 10.1109/TCPMT.2013.2297734.
(Continued)

*Primary Examiner* — Eun Hwa Kim
(74) *Attorney, Agent, or Firm* — Kaplan Breyer Schwarz, LLP

(57) ABSTRACT

A probe suitable for deep-brain recording and stimulation is provided. The probe comprises a wire bundle that includes a plurality of wires, an integrated circuit having a plurality of electrodes, and an interposer that joins the wire bundle and the integrated circuit such that each of the plurality of electrodes is electrically connected with a different wire of the plurality of wires.

18 Claims, 13 Drawing Sheets

(51) Int. Cl.
*A61N 1/05* (2006.01)
*A61B 5/0478* (2006.01)
*A61N 1/36* (2006.01)

(52) U.S. Cl.
CPC .... *A61N 1/0534* (2013.01); *A61B 2562/0209* (2013.01); *A61N 1/36067* (2013.01)

(56) References Cited

U.S. PATENT DOCUMENTS

| | | | | |
|---|---|---|---|---|
| 8,798,737 | B2* | 8/2014 | Merz | A61N 1/0531 607/116 |
| 2004/0006264 | A1* | 1/2004 | Mojarradi | A61B 5/0478 600/378 |
| 2012/0109262 | A1 | 5/2012 | Martens | |
| 2013/0030500 | A1 | 1/2013 | Toader et al. | |
| 2014/0309548 | A1 | 10/2014 | Merz et al. | |
| 2014/0330354 | A1* | 11/2014 | Shelton | A61N 1/0551 607/116 |

OTHER PUBLICATIONS

Johnson et al., "A novel high electrode count spike recording array using an 81,920 pixel transimpedance amplifier-based imaging chip", "Journal of Neuroscience Methods", 2012, pp. 223-232, vol. 205, No. 2, Publisher: Elsevier; doi:10.1016/j.jneumeth.2012.01.003.

Schaefer, et al., "A scalable approach to neuronal recording and stimulation"; Publisher: Association of University Technology Managers (AUTM); http://gtp.autm.net/network/stanford-university/technology/view/69109.

Skeath et al., "Electroformed Microelectrode Array for a Human Retinal Prosthesis Interface"; Publisher: http://test.electrochem.org/dl/ma/206/pdfs/2576.pdf.

Hajjhassan et al., "NeuroMEMS: Neural Probe Microtechnologies", "Sensors", 2008, pp. 6704-6726, vol. 8, No. 10, Publisher: www.mdpi.com/journal/sensors; DOI: 10.3390/s8106704; ISSN 1424-8220.

Angle, et al, "Recording Neuronal Electrical Activity Using Solid-Conductor Intracellular Nanoelectrodes (SCINEs)", "PloS one", Aug. 15, 2012, p. e43194, vol. 7, No. 8, Publisher: Public Library of Science; doi: 10.1371/journal.pone.0043194.

Scribner et al., "A Retinal Prosthesis Technology Based on CMOS Microelectronics and Microwire Glass Electrodes", "Transactions on Biomedical Circuits and Systems", Mar. 2007, pp. 73-84, vol. 1, No. 1, Publisher: IEEE; doi: 10.1109/TBCAS.2007.893186.

\* cited by examiner

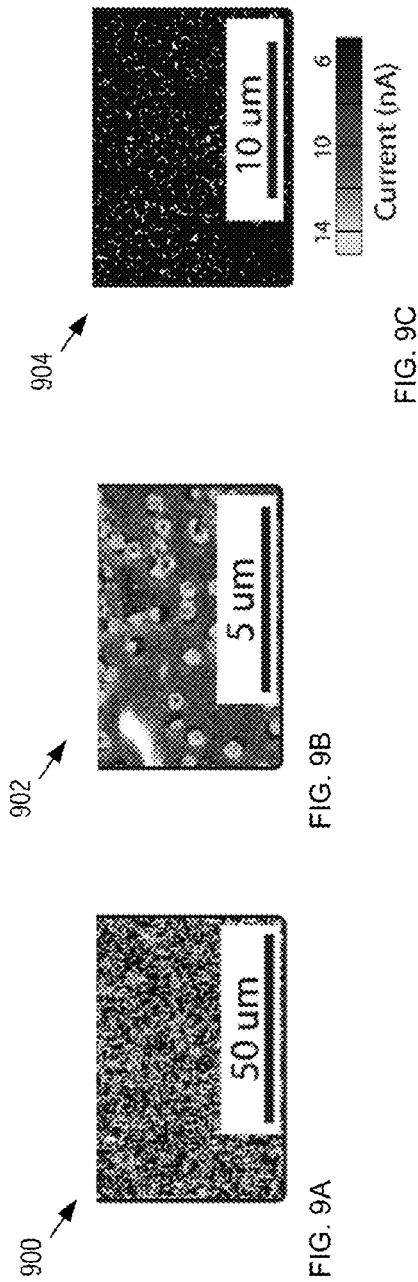
FIG. 9A
FIG. 9B
FIG. 9C
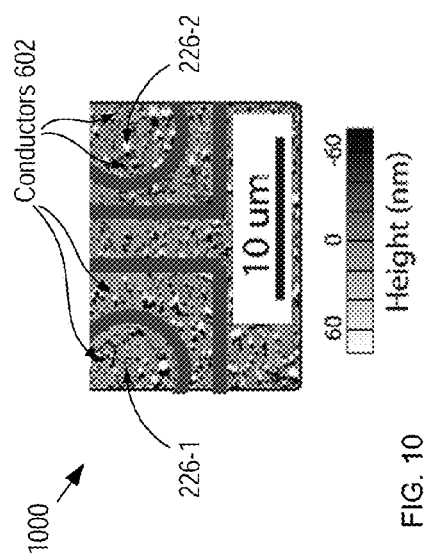
FIG. 10

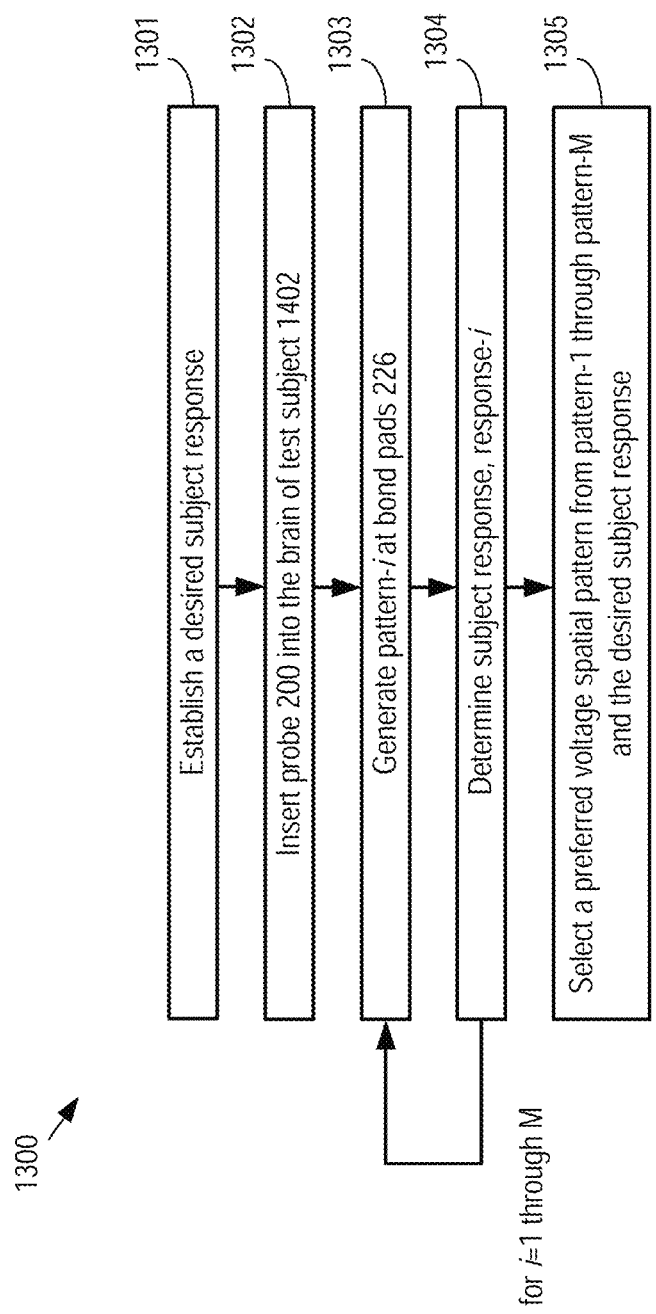

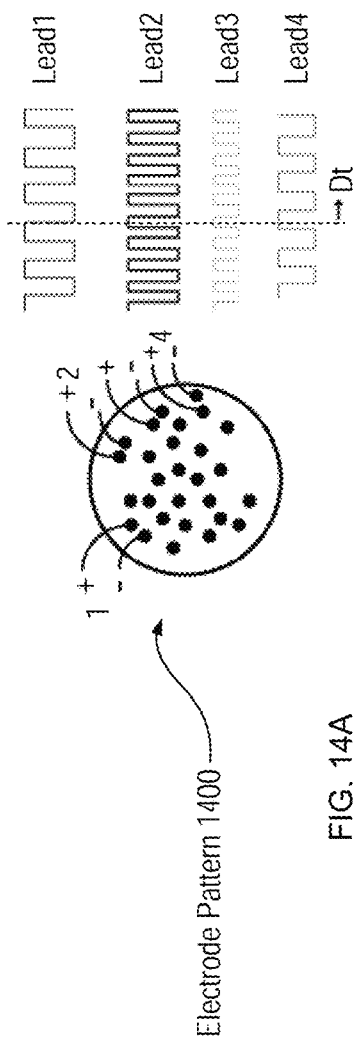
FIG. 14A
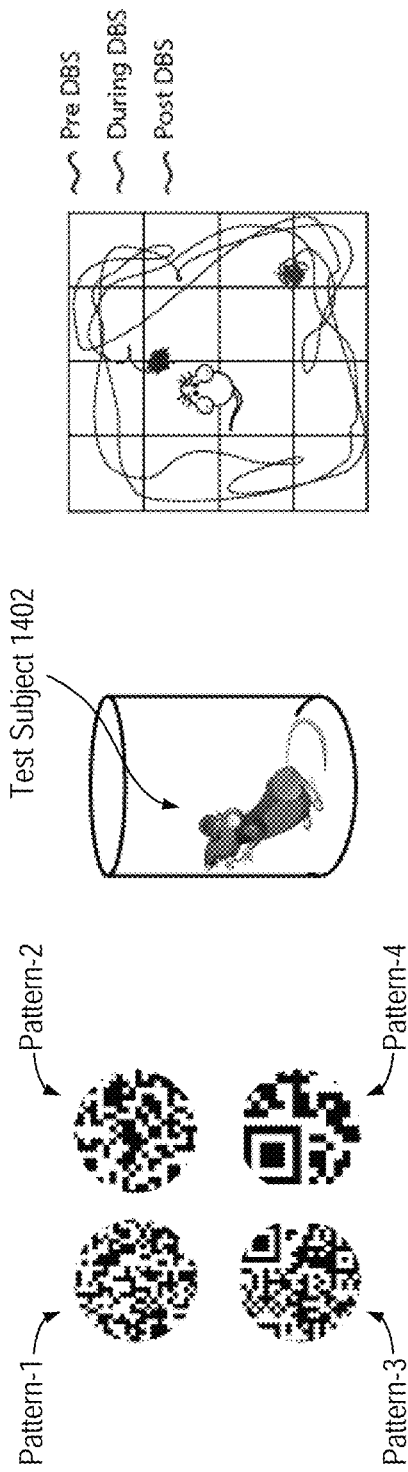
FIG. 14B
FIG. 14C
FIG. 14D

DEEP-BRAIN PROBE AND METHOD FOR RECORDING AND STIMULATING BRAIN ACTIVITY

CROSS REFERENCE TO RELATED APPLICATIONS

This case claims priority of U.S. Provisional Patent Application Ser. No. 62/077,552, filed Nov. 10, 2014, which is incorporated herein by reference. If there are any contradictions or inconsistencies in language between this application and one or more of the cases that have been incorporated by reference that might affect the interpretation of the claims in this case, the claims in this case should be interpreted to be consistent with the language in this case.

FIELD OF THE INVENTION

The present invention relates to neural probes in general, and, more particularly, to deep-brain probes for stimulating and recording neural activity.

BACKGROUND OF THE INVENTION

An improved understanding of the brain is considered a key to the continued advancement of modern medical technology and, therefore, human health and well-being. But, its scale (100 billion neurons) and density of connections (1 neuron connecting to many thousands) present experimental challenges for designing neural interfaces. Getting information into and out of its neural networks requires an ability to access the activity of many thousands of neurons simultaneously, which requires a commensurately high number of individual recording channels and electrodes. The technology for practical electrical recording in the brain has not significantly advanced in decades, however, and the limited number of channels (≤1000) in state of the art neural probes is a limiting factor for understanding brain function.

A better understanding of brain functionality would also enable improved treatment of many neurological diseases, such as Parkinson's disease. Deep-brain stimulation (DBS) is currently used to stimulate specific parts of the brain (e.g., basal ganglia nuclei, such as the subthalamic nucleus or internal part of the globus pallidus, etc.) with electrical impulses via a surgically implanted probe containing one or more electrodes. Unfortunately, the effectiveness of conventional DBS methods is limited by the available probe technology. Currently available therapeutic DBS probes normally include only one or a few electrodes. While such a probe enables control of stimulation frequency and amplitude, it provides little or no control over the spatial pattern of the excitation signals—in contrast to the present understanding of the manner in which neural circuits process information. In addition, single-electrode probes cannot provide the nuanced intervention desirable for the treatment of complex neuropsychiatric disorders, such as individually activating corticofugal axons with highly localized stimulation.

As a result, to understand and treat diseases such as Parkinson's, depression, and post-traumatic stress disorder, and the like, a more sophisticated stimulation method that can deliver patterned excitation over a fairly large region to deep brain areas is needed—ideally with single-cell-level resolution. Multi-electrode probes are seen as a means for providing such capability. To that end, significant effort is being directed toward the development of high-density electrode arrays, such as comb-like arrangements of silicon microelectrodes and flat lithography-based nano-electrode arrays.

Silicon microelectrodes are sculpted from conventional silicon wafers, which are normally used for planar fabrication of integrated circuits. A typical silicon microelectrode includes a dense array of electrodes arranged along the length of each "tooth" of the comb. These probes are capable of dense neural sampling along the longitudinal axis of each tooth; however, they are bulky. In addition, due to fabrication-based limitations on the aspect-ratio with which the probe elements can be made, it is difficult, if not impossible, to make a silicon comb with teeth that are both long enough and fine enough to densely sample neurons within a useful volume of brain tissue. Still further, these arrays are typically limited to approximately one hundred channels, which enables access to only about 0.5% of the cells in a single cortical circuit.

Lithographically fabricated nano-electrode arrays can have submicron pitch, which affords good lateral sampling density. In similar fashion to silicon electrodes, however, the aspect ratio limitations for such nanowires prove limiting. Growing oriented nanowires of >100 micrometers in length is extremely difficult. As a result, without invasive surgery, such shallow electrode structures enable recording from only those neurons that are located on, or very near, the surface of the brain.

A practical, high-density, massively parallel, single-cell-resolution probe that can access to deep-brain activity would be revolutionary for neurophysiology. It would enable an improved fundamental understanding of neural-network behavior, as well as improved deep-brain stimulation treatments. Such a probe, however, remains unrealized in the current state of the art.

SUMMARY OF THE INVENTION

The present invention enables massively parallel electrical interaction with deep brain tissue. It is a highly scalable technology that enables probes having greater than 100,000 channels with potentially high sampling density (50-micron pitch or better), and that are usable at insertion depths greater than 2 millimeters without requiring surgical implantation. Embodiments of the present invention are operative for interfacing with hundreds of thousands of neurons via bundles of wires, each having an electrode disposed near a free end, where the free ends of the wires are dimensioned and arranged to splay out into a three-dimensional arrangement during insertion into a brain. Embodiments of the present invention are particularly well suited for use in basic brain research applications, as well as clinical applications, such as neuroprosthetics and deep-brain-stimulation treatments for neurological and psychiatric diseases.

In some embodiments, wires of the bundle are electrically connected with an integrated circuit through an interposer having myriad conductive paths through its thickness, where the conductive paths have an inter-path spacing that is different than the pitch of the bond pads of the integrated circuit, and preferably smaller than the width of the bond pads. As a result, the interposer mitigates alignment issues that would otherwise make connecting a wire bundle having thousands of wires to an integrated circuit difficult, if not impossible. In some embodiments, a portion of each wire projects from a fixed end of the wire bundle to form a "bed of nails" that can be joined to the bond pads of the integrated circuit, with or without an intervening interposer. In such embodiments, it is preferable that the wires of the wire bundle are arranged in an arrangement having an inter-wire spacing that is different from than the pitch of the bond pads and, ideally, smaller than the width of the bond pads.

An illustrative embodiment of the present invention is a deep-brain probe that includes a wire bundle containing thousands of individual insulated wires. Each of the wires has a fixed end and these are joined together to collectively define a first surface. An electrode is disposed at a free end of each wire such that the electrodes are free to move independently and splay out as the probe is inserted into the brain enabling the electrodes to collectively define a three-dimensional pattern of electrodes within the neural matter of the brain. The wire bundle is electrically connected to a high-density, CMOS-based, LED-display-driver integrated-circuit chip via an anisotropically conductive interposer. The integrated-circuit chip includes a two-dimensional arrangement of bond pads on which spatial patterns of voltages can be realized. The wire bundle is electrically connected to the integrated-circuit chip by an interposer that includes an electrically insulating body and a plurality of electrically conductive paths through its thickness. As a result, the interposer is an anisotropic conductor that provides electrical conductivity along the conductive paths but not in the regions between them. The spacing of the conductive paths is smaller than the width of the bond pads on the integrated-circuit chip, which mitigates alignment issues when assembling the probe. In some embodiments, the spacing of the conductive paths is non-uniform in at least one dimension. In some embodiments, the conductive paths are arranged in high-density groups that are arranged in a two-dimensional arrangement. In some embodiments, the conductive paths are arranged in an array having a uniform pitch in at least one dimension.

The body of the interposer is a multi-layer stack that includes an interior layer of a first material that is more compressible than both the integrated-circuit chip and the wire bundle. The interior layer is sandwiched between a pair of surface layers made of a second material that has high tensile strength but is also flexible. As a result, the interposer facilitates contact between the CMOS chip and bundle surfaces by accommodating any non-planarity and/or topography that might exist at either the wire bundle surface or the surface of the integrated-circuit chip; however, it is also strong and robust to mitigate breakage of the layer. In some embodiments, the body of the interposer comprises a single layer of compressible material. In some embodiments, the interposer comprises a track-etched membrane that includes a plurality of conductive nanowires formed by electroplating within the pores of the membrane.

In some embodiments, the wire bundle includes at least one optical fiber that enables imaging and/or optical detection within the brain, or facilitates optical alignment between the CMOS chip and wire bundle.

In some embodiments, at least one of the wires of the bundle has a micron-scale cross-sectional dimension. In some embodiments, at least one of the wires of the bundle has a nanometer-scale cross-sectional dimension.

An embodiment of the present invention is a deep-brain probe comprising: a wire bundle comprising a first plurality of wires that are arranged in a first two-dimensional arrangement, wherein each of the first plurality of wires has a first end and a second end, and wherein each of the first plurality of wires includes: a core that is electrically conductive; an electrical insulator that surrounds the core along the length of the wire; and an electrode that is electrical-insulator-free; wherein the wire bundle has a first portion in which the first plurality of wires is mechanically joined together to collectively define a stalk, the first end of each wire of the plurality thereof terminating at a first surface of the stalk; and wherein the wire bundle has a second portion in which each wire of the first plurality thereof is unrestrained, the second end and the electrode of each wire of the plurality thereof being in the second portion; and a first integrated circuit comprising a plurality of bond pads that is arranged in a second two-dimensional arrangement; wherein the wire bundle and the first integrated circuit are arranged such that each of the plurality of bond pads is electrically connected with one or more wires of the first plurality thereof, and wherein each electrical connection is established via an elastically deformable element.

BRIEF DESCRIPTION OF THE DRAWINGS

FIGS. 9A-B depict scanning-electron microscope (SEM) pictures, at different magnifications, of a region of interposer 204.

FIG. 9C depicts a conductivity map of interposer 204.

FIG. 10 depicts an overlap showing outlines of bond pads of IC 206 overlaid on the surface of interposer 204.

FIG. 13 depicts operations of a method for interfacing with a brain in accordance with the illustrative embodiment of the present invention.

FIG. 14A depicts a two-dimensional cross-section of a three-dimensional electrode pattern that manifests in the brain of a subject patient.

FIG. 14B depicts four examples of stimulation patterns attainable with a probe in accordance with the present invention.

FIGS. 14C-D depict examples of tests for motor behavior of a mouse model as enabled by the present invention.

DETAILED DESCRIPTION

Figure 1:
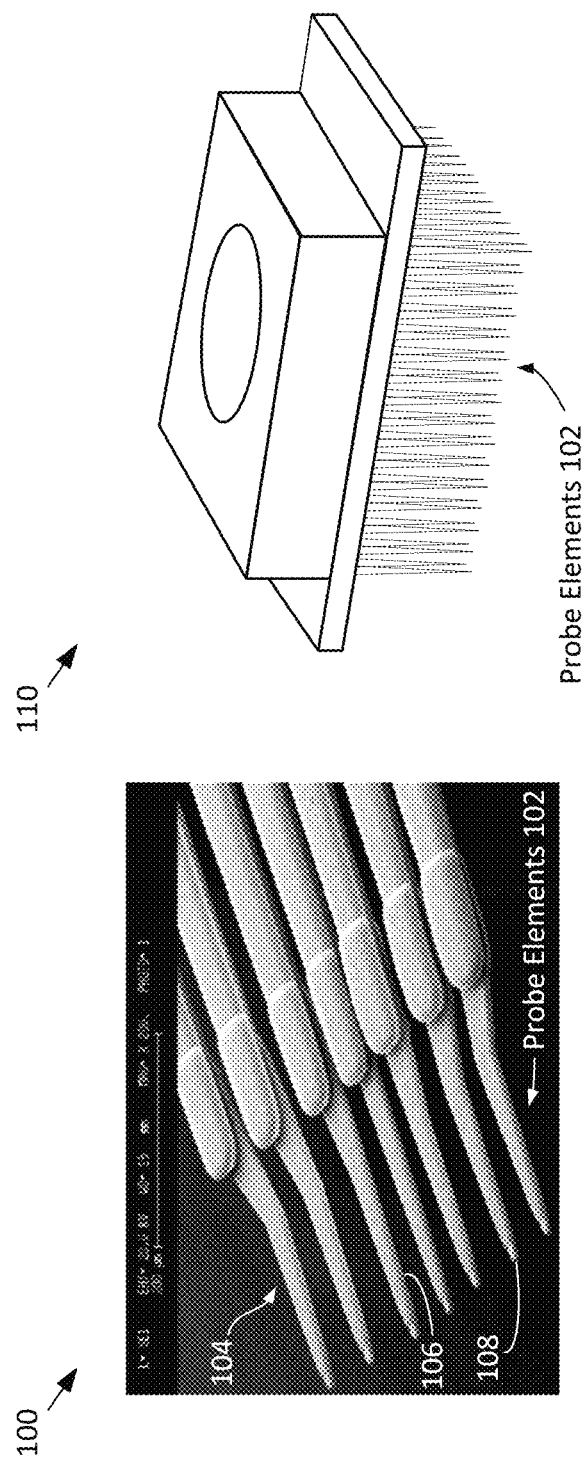
FIG. 1A depicts a picture of a first neural probe in accordance with the prior art.
FIG. 1B depicts a picture of a second neural probe in accordance with the prior art.

FIG. 1A depicts a picture of a first neural probe in accordance with the prior art. Probe 100 is a one-dimensional array of metal-wire-based neural probe elements.

Each probe element 102 includes metal shaft 104 and insulation layer 106. Metal shafts 104 are defined on a conventional planar-processing substrate (e.g., a silicon wafer) via conventional photolithography and metal deposition processes, such as electroplating. Once formed, a portion of each of metal shafts 104 is released by etching away of the substrate material on which it is disposed and coated with an electrically insulating material, such as Parylene-C or silicon nitride, to form insulation layer 106. Electrode 108 is then exposed by removal of the insulator material at the tip of the metal structure. Although not shown in FIG. 1A, probe elements 102 extend from a base platform on which bond pads are formed. These bond pads can be readily attached to matching bond pads of an integrated circuit, such as a signal processor chip, using conventional bump-bonding techniques.

FIG. 1B depicts a picture of a second neural probe in accordance with the prior art. Probe 110 is a two-dimensional array of silicon-based neural probe elements.

Probe 110 is fabricated using an ethylene diamine pyrocatechol (EDP)-based anisotropic etch and a boron etch stop to sculpt probe elements 112 from the bulk of a silicon substrate. A suitable metal, such as gold, platinum, or iridium, is then deposited and patterned to define recording sites and an insulation layer is formed on top of silicon substrate. Finally, connection is made to the probe elements with polysilicon cables. Unfortunately, these polysilicon cables are relatively fragile and have a tendency to break—particularly for lengths greater than a few millimeters.

Although probes 100 and 110 have been successfully employed in some applications, they suffer from several disadvantages. For example, due to fabrication-based limitations on the aspect-ratio of the probe elements, it is difficult to fabricate probes elements that are both long enough to sample neurons within brain targets that are deeper than 1 mm while still being dense enough to record from many cells.

It is an aspect of the present invention that the use of a wire bundle having one thousand or more individually addressable wires enables a deep-brain probe that can interface with neural matter in a more useful manner than enabled by the prior art. Further, the present invention enables the wires of such a wire bundle to be electrically interconnected with an integrated circuit that can stimulate and/or monitor brain activity in a more sophisticated manner than possible with prior-art brain probes.

It should be noted that the present invention enables significant improvement over probes known in the prior art. Specifically, the present invention enables deep-brain probes having the highest resolution and number of independent electrodes ever developed for any type of electrical brain interface. By comparison, the very latest reported high density prior-art electrical recording devices have approximately 1024 electrodes, two orders less than enabled by the present invention.

As a result, it is another aspect of the present invention that these probes enable revolutionary therapeutic strategies using DBS, with broad impact on current DBS design and translational value for clinical application. Unlike a conventional DBS electrode, these microwires can be provide multi-site, spatially controlled stimulation, where stimulation frequency and amplitude of each electrode can be individually fine-tuned. Secondly, this enables design of the DBS stimulation protocol to fit the needs of individual patients, providing new means for personalized treatment. Thirdly, compared to prior-art electrode arrays, probes in accordance with the present invention provide higher electrode number and density that could control activity of a significant fraction of the cells or passing axonal fibers in the network over a fairly large subthalamic nucleus region. One skilled in the art will recognize that this has been long sought in clinical practice.

Figure 2:
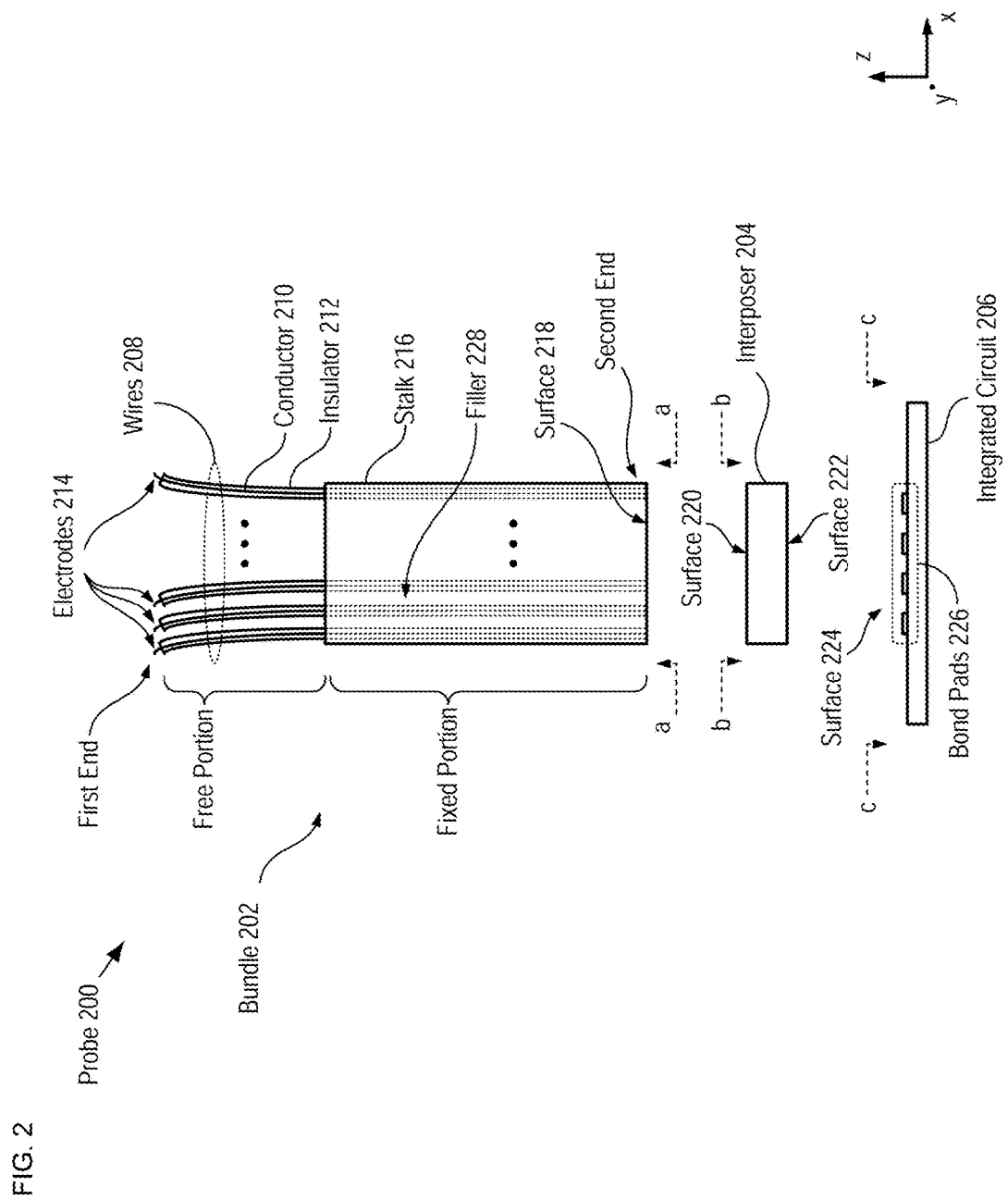
FIG. 2 depicts a schematic drawing of an exploded diagram of a deep-brain probe in accordance with an illustrative embodiment of the present invention.

FIG. 2 depicts a schematic drawing of an exploded diagram of a deep-brain probe in accordance with an illustrative embodiment of the present invention. Probe 200 includes bundle 202, interposer 204, and integrated circuit 206.

Figure 3:
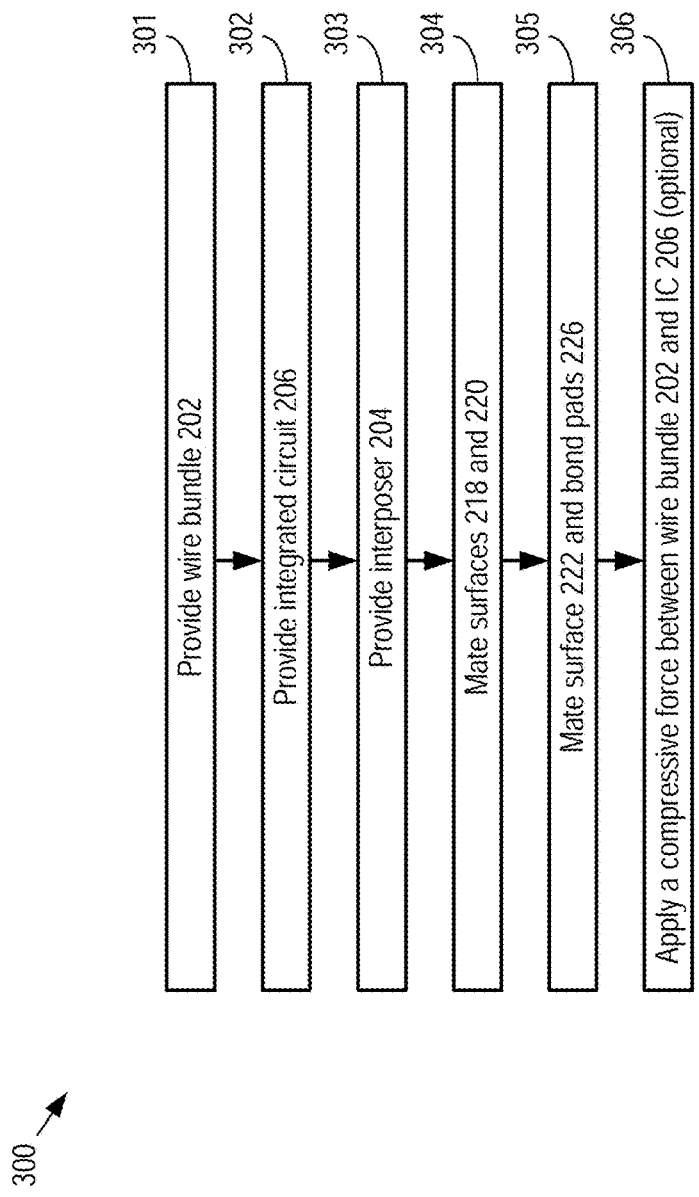
FIG. 3 depicts operations of a method for forming a deep-brain probe in accordance with the illustrative embodiment.

FIG. 3 depicts operations of a method for forming a deep-brain probe in accordance with the illustrative embodiment. Method 300 begins with operation 301, wherein wire bundle 202 is provided.

Bundle 202 is a collection of N individual insulated wires 208. In the depicted example, N is equal to 100,000; however, in some embodiments N is another practical number (preferably greater than a few thousand). Each of wires 208 includes a conductor 210 (i.e., a core), which is individually encased in insulator 212 along its length. In the depicted example, conductors 210 comprise gold and insulator 212 is glass; however, in some embodiments, the conductors and or the insulator comprises another conventional material suitable for insertion into neural matter. Materials suitable for use in conductors 210 include, without limitation metals (e.g., copper, gold, platinum, etc.), semiconductors, conductive polymers, composite materials, and the like. Materials suitable for use in insulator 212 include, without limitation, other glasses, silicone compounds (e.g., polydimethylsiloxane (PDMS), poly(methyl methacrylate) (PMMA), etc.), medical-grade epoxies, organic polymer encapsulants, composite materials, and the like. In the illustrative embodiment, wires 208 are formed by a thermal drawing process; however, in some embodiments, wires 208 are formed via a different conventional process (e.g., carbon-based fibers having a chemically deposited insulation). In some embodiments, insulation 212 comprises a plurality of electrically insulating layers. In some of these embodiments, the different insulating layers have one or more different properties, such as dielectric constant, chemical reactivity/resistance, and the like.

In the depicted example, each of conductors 210 has a cross-sectional diameter of approximately 10 microns. In some embodiments, at least some of conductors 210 has a nanometer-scale cross-sectional diameter. In some embodiments, one or more of conductors 210 has a different micron-scale cross-sectional diameter. Further, in some embodiments, bundle 202 includes at least one optical fiber in addition to wires 208, where the optical fiber is operative for enabling imaging of the neural matter into which probe 200 is inserted.

Wire bundle 202 includes a fixed portion and a free portion. In its fixed portion, wires 208 are mechanically fixed together via filler material 228 to collectively define stalk 216, which is substantially rigid. In the free portion of bundle 202, the wires are unrestrained. For the purposes of this Specification, including the appended claims, the term "unrestrained" is defined as meaning not joined together. For example, within free portion of bundle 202, each of wires 208 is free to move independently relative to the other wires, even though one or more of the wires can abut another wire within the free portion. In some embodiments, the lengths of the wires 208 in the free portion of bundle 202 are non-uniform. In some embodiments, the lengths of the wires 208 in the free portion of bundle 202 are uniform.

It is an aspect of the present invention that a brain probe that includes wire bundle comprising a plurality of individual wires enables the wires to have an arbitrarily long length. As a result, brain probes in accordance with the present invention can be used to interface with neural matter deep within a brain without requiring the invasive surgery necessary to implant prior-art probes and prostheses, such as those disclosed by Scribner, et al., in "A Retinal Prosthesis Technology Based on CMOS Microelectronics and Microwire Glass Electrodes, *IEEE Trans. on Biomedical Circuits and Syst.*, Vol. 1, pp. 73-84 (2007). Further, because probes in accordance with the present invention include wire bundles having a portion in which the individual wires are mechanically independent, as the probe is inserted into a brain, the free portion of each wire responds independently to force imparted on it. This gives rise to a dense three-dimensional arrangement of electrodes in the brain after deployment, which enables more sophisticated recording and/or stimulation of neural activity.

At the first (i.e., free) end of each wire 208, the end face of conductor 210 is exposed, thereby defining an electrode 214, which is free to move independently from all other electrodes 214 as probe 200 is inserted into a brain. In some embodiments, a portion of insulator 212 is also removed at the free end of each wire to enlarge electrode 214. In some embodiments, electrodes 214 are electrochemically coated with a low-impedance coating, such as iridium oxide (or other transition-metal oxide, such as $MnO_2$, etc.), a conductive polymer (e.g., PEDOT, etc.), or a material promoting a high surface area (e.g. carbon nanotubes, platinum black, nanoparticle composites, and the like). Such surface modification decreases the interfacial electrical impedance between the exposed conductor material and brain tissue, thereby enabling more sensitive neural-activity recording.

At the fixed end of bundle 202, the second end of each of wires 208 terminates at surface 218. The joined portions of wires 208 collectively form stalk 216, which has a substantially circular cross-sectional shape. Stalk 216 provides mechanical strength over a length suitable for enabling insertion of the probe deep into a brain. In the illustrative embodiment, stalk 216 has a diameter of approximately 1 millimeter (mm), which is comparable to prior-art deep-brain probes. In some embodiments, stalk 216 has a different cross-sectional diameter based on the size of the brain area to be sampled and the desired sampling density.

Figure 4A:
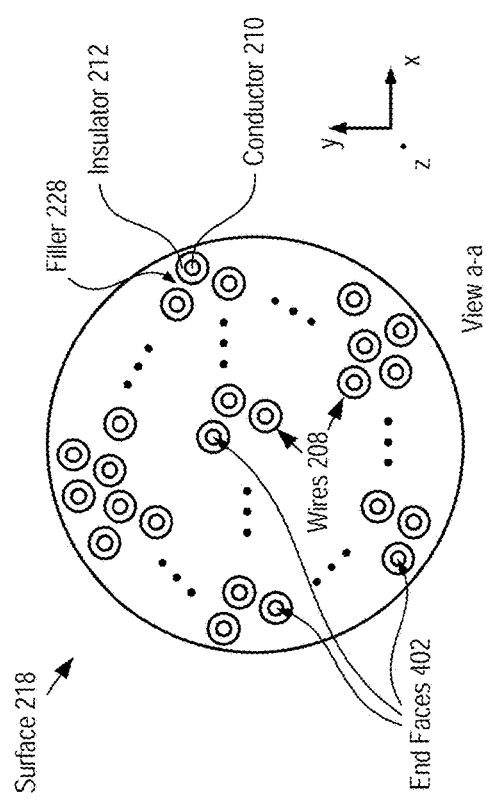
FIGS. 4A and 4B depict a schematic drawing and an electron micrograph, respectively, of surface 218 of wire bundle 202.
Figure 4B:
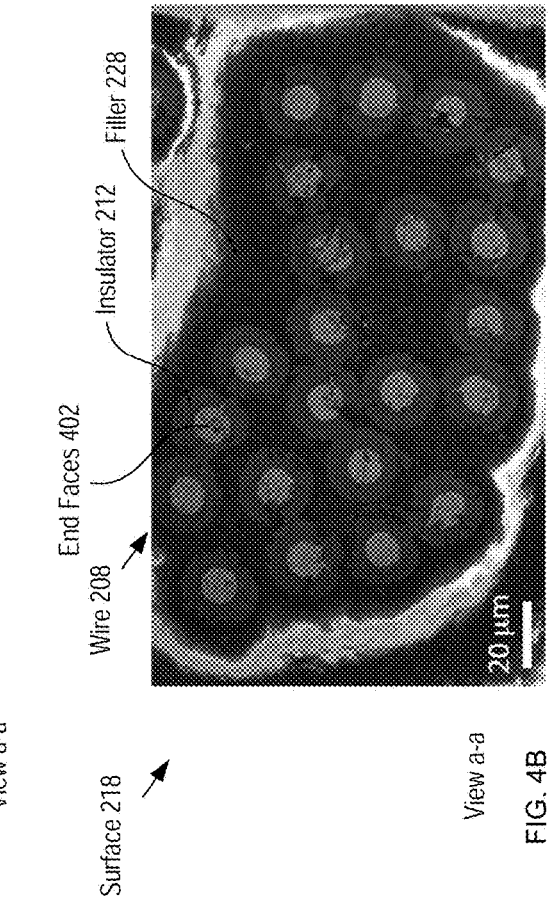

FIGS. 4A and 4B depict a schematic drawing and an electron micrograph, respectively, of surface 218 of bundle 202.

Within stalk 216, wires 208 are embedded in filler 228, which provides mechanical strength and facilitates polishing surface 218. In the depicted example, filler 228 is an acrylic resin; however, one skilled in the art will recognize, after reading this Specification, that myriad materials exist that are suitable for use as filler 228 without departing from the scope of the present invention.

The spacing between wires 208 at surface 218 varies but is generally within the range of a few microns to approximately 20 microns (although some wires can be in contact with a neighboring wire). In some embodiments, wires 208 are spaced by a different inter-wire spacing at surface 218.

Stalk 216 is polished flat at surface 218 to reveal end faces 402 of conductors 210, which collectively define an array of contactable metal surfaces that enable electrical connection with integrated circuit 206 via interposer 204. In the depicted example, filler 228 is etched back at surface 218 such that a portion of each of conductors 214 projects outwardly from the face of the filler. Typically, the filler is relieved from end faces 402 by only a few microns; therefore, stalk 216 remains mechanically robust.

At operation 302, integrated circuit (IC) 206 is provided.

Figure 5:
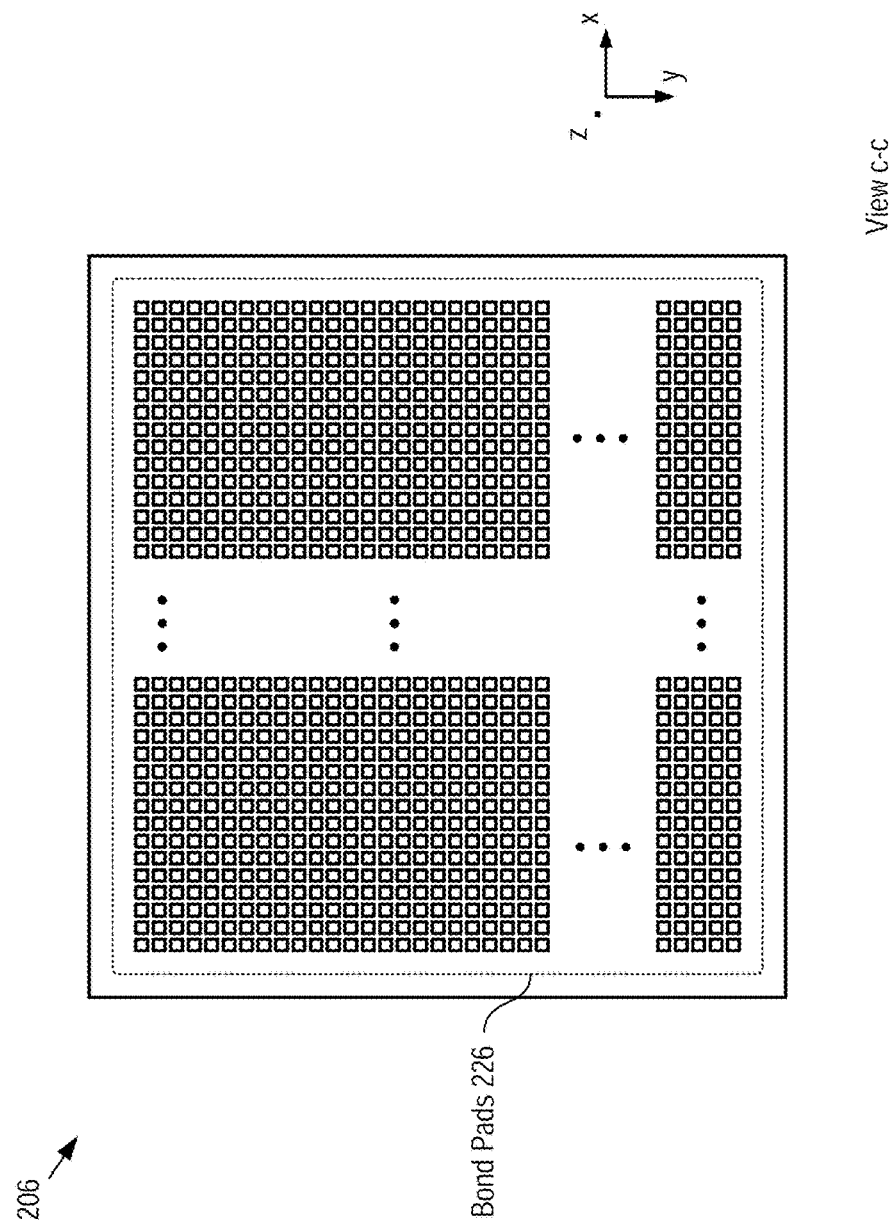
FIG. 5 depicts a schematic drawing of surface 224 of IC 206.

FIG. 5 depicts a schematic drawing of surface 224 of IC 206. In the depicted example, IC 206 is a conventional display driver chip, such as might be used to drive an LED-based or LCD-based display. IC 206 includes an 800×600 two-dimensional array of individually addressable bond pads 226, each of which is operative for driving a pixel of a conventional display. Each of bond pads 226 is substantially square with sides of approximately 10 microns. Bond pads 226 are arranged in a two-dimensional array having a pitch in each dimension of approximately 15 microns. This inter-bond-pad spacing is well matched to the conductor spacing for the wires of bundle 202, as well as the cell spacing in the brain. Although in the illustrative embodiment, IC 206 is operative for driving a display, it will be clear to one skilled in the art, after reading this Specification, how to specify, make, and use alternative embodiments wherein IC 206 provides a different desired functionality. For example, in some embodiments, IC 206 is operative for at least one of:

i. providing one or more voltages; or ii. measuring one or more voltages; or iii. sensing one or more electric currents; or iv. providing one or more electric currents; or v. sensing one or more other electrical parameters (e.g., capacitance, inductance, impedance, etc.); or vi. establishing electric fields between one or more electrode pairs; or vii. any combination of i, ii, iii, iv, v, and vi.

One skilled in the art will recognize that the functionality of IC 206 is a matter of design choice that is typically based on the needs for the application for which probe 200 is intended.

Further, one skilled in the art will recognize, after reading this Specification, that the dimensions, array sizes, wire sizes, and stalk dimensions provided herein are merely exemplary and that any one or more of these physical characteristics can be changed to another practical value without departing from the scope of the present invention. Still further, one skilled in the art will recognize that bond pads 226 can be arranged in any two-dimensional arrangement, with or without periodicity in either dimension.

It should be noted that a principle challenge for forming probe 200 is joining bundle 202 and IC 206 in such a manner that a large fraction (preferably, all) of conductors 208 are electrically active and in electrical communication with circuit elements of the integrated circuit. Given the sheer number of electrical connections between the wire bundle and the integrated circuit, as well as the extremely small size of wires 208, the use of conventional soldering methods is impractical. Further, the unwieldy nature of the wire bundle and the substantially random locations of end faces 402 at surface 218 makes the use of conventional solder-bump bonding between the components difficult, if not impossible.

It is an aspect of the present invention that high-quality, low-cost, practical electrical connection between bundle 202 and IC 206 can be established by joining them via an anisotropically conductive interposer having a plurality of finely spaced conductors that are operative for conducting electrical signals in the z-direction (as depicted in FIG. 2), where the conductors are embedded in an electrically insulating body that precludes electrical conduction in directions other than the z-direction. Further, it is preferable that the finely spaced conductors are characterized by an inter-conductor spacing within the interposer that is smaller than the size of the bond pads of the integrated circuit, the probability that each bond pad will be electrically connected to at least one wire of the wire bundle is increased, thereby mitigating the challenges inherent to aligning wires 208 and bond pads 226 during assembly of probe 200. It should be noted, however, that an inter-conductor spacing that is different than each of the inter-wire spacing of wire bundle 202 and the bond-pad spacing of IC 206 ensures that a high percentage of wires 208 are electrically connected with bond pads 226 while simultaneously easing alignment requirements. The use of such an interposer to electrically connect bundle 202 and IC 206, therefore, enables patterned electrical stimulation deep in the brain in a convenient and cost-effective manner. It should be noted, however, that in some embodiments, the spacing of wires 208 and/or conductors 604 is matched to that of bond pads 226. In some of these embodiments, each of wires 208 and bond pads 226 are arranged in a two-dimensional ordered array having constant pitch in each dimension.

At operation 303, interposer 204 is provided. Interposer 204 is a compressible anisotropic conductor that facilitates good electrical contact between conductors 210 and bond pads 226. It should be noted that, in the context of this Specification, including the appended claims, compressible elements are elastically deformable. In other words, compressible elements deform substantially elastically.

Figure 6:
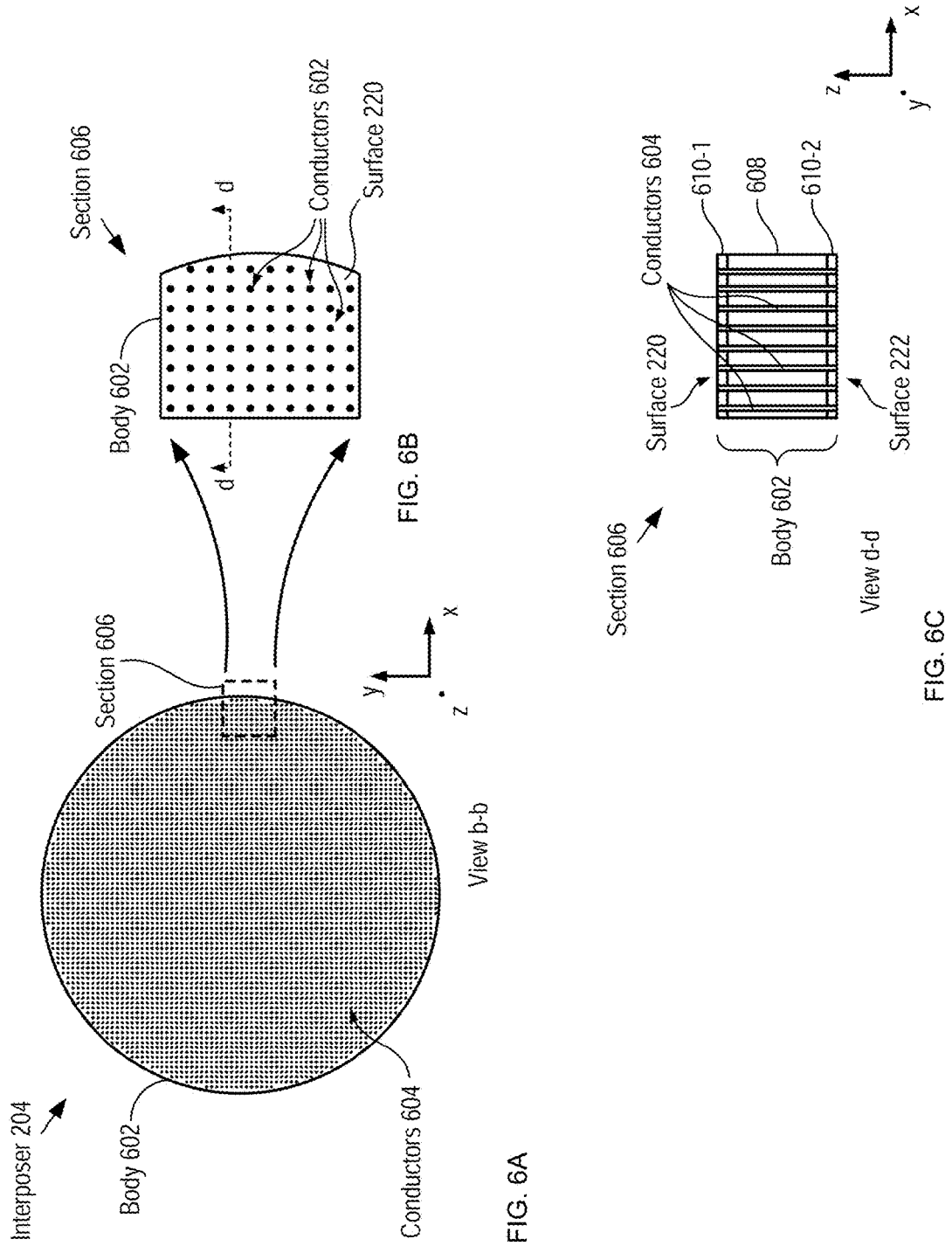
FIG. 6A depicts a schematic drawing of a top view of an interposer in accordance with the illustrative embodiment.
FIGS. 6B and 6C depict schematic drawings of enlarged top and cross-sectional views, respectively, of a region of interposer 204.

FIG. 6A depicts a schematic drawing of a top view of an interposer in accordance with the illustrative embodiment. Interposer 204 includes body 602 and conductors 604.

FIGS. 6B and 6C depict schematic drawings of enlarged top and cross-sectional views, respectively, of a region of interposer 204. The view shown in FIG. 6C is taken through line d-d of FIG. 6B.

Figure 7:
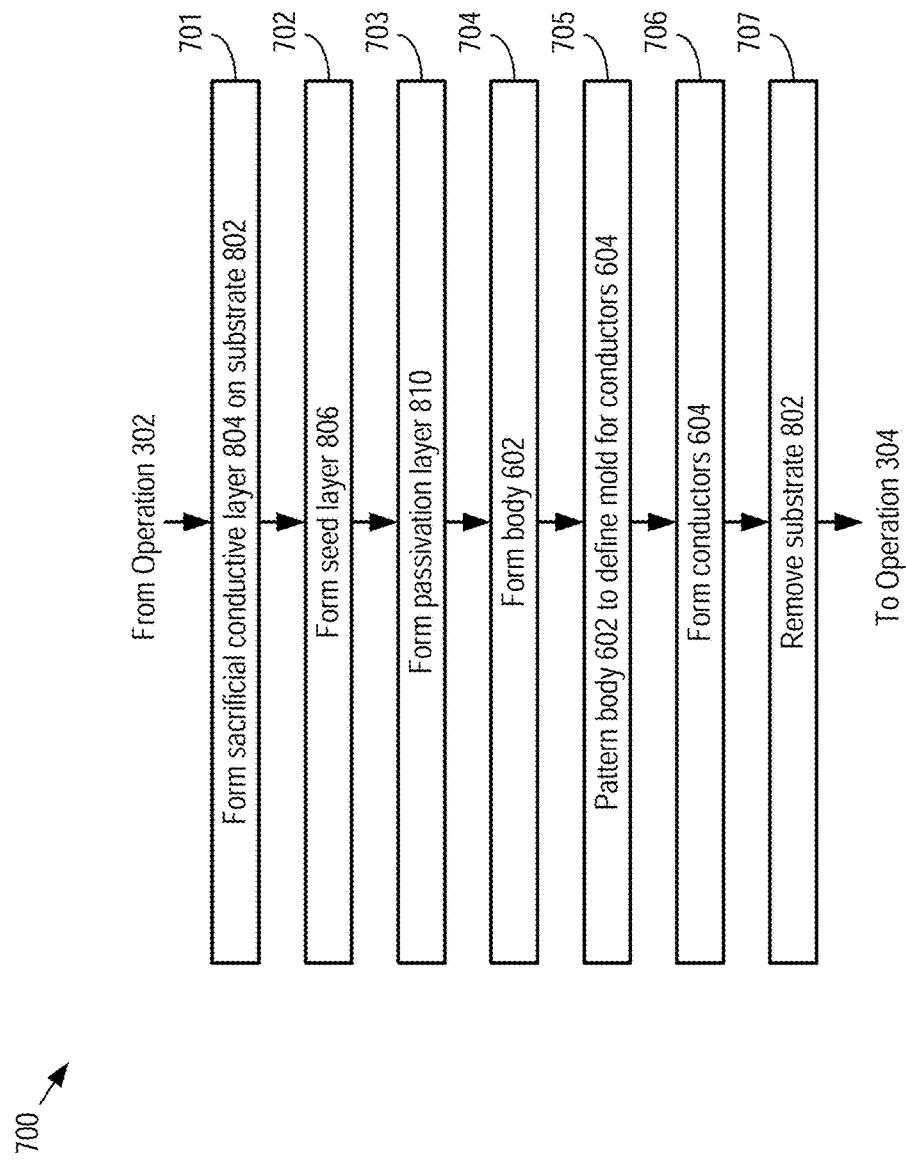
FIG. 7 depicts sub-operations of a sub-method suitable for use as operation 303.

FIG. 7 depicts sub-operations of a sub-method suitable for use as operation 303. Sub-method 700 is described with continuing reference to FIGS. 6A-C, as well as reference to FIGS. 8A-D.

FIGS. 8A-D depict schematic drawings of cross-sectional views of a portion of interposer 204 at different points of its fabrication in accordance with the illustrative embodiment of the present invention.

Sub-method 700 begins with sub-operation 701, wherein sacrificial layer 804 is formed on substrate 802. Sacrificial layer 804 is a layer of electrically conductive material that can be selectively etched to separate interposer 204 from substrate 802 once the interposer has been fully fabricated. In the depicted example, sacrificial layer 804 is a layer of titanium having a thickness of a few nanometers (nm) disposed on a conventional silicon substrate suitable for planar processing; however, other materials can be used for either of sacrificial layer 804 or substrate 802 without departing from the scope of the present invention.

At sub-operation 702, seed layer 806 is formed on sacrificial layer 804. Seed layer 806 includes a plurality of regions 808, which are physically separated from one another within the seed layer. In the depicted example, each region 808 is a substantially circular region comprising gold and has a diameter of approximately 3 microns and a thickness of approximately 20 nm.

At sub-operation 703, passivation layer 810 is a layer of alumina having a thickness of approximately 50 nm. In some embodiments, passivation layer has a different thickness within the range of approximately 30 nm to approximately 250 nm. Passivation layer 810 is formed as a blanket layer via atomic-layer deposition and subsequently patterned using an appropriate etch (preferably a dry etch, such as RIE) to expose a portion of each region 808 but leaving passivation material in the open areas between regions 808. Passivation layer 810 is included, in part, to inhibit the growth of electrical conductor between regions 808 during the subsequent formation of conductors 604 via electroplating, as discussed below. In some embodiments, passivation layer 810 comprises a different electrically insulating material (e.g., silicon nitride, silicon oxide, etc.) and/or is deposited via a different conventional deposition technique, such as plasma-enhanced chemical vapor deposition (PECVD), and the like.

Figure 8A:
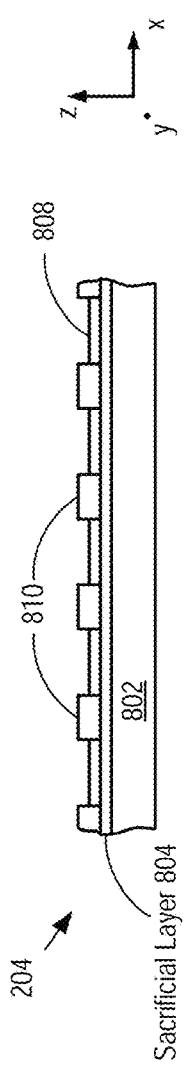
FIGS. 8A-D depict schematic drawings of cross-sectional views of a portion of interposer 204 at different points of its fabrication in accordance with the illustrative embodiment of the present invention.

FIG. 8A depicts interposer 204 after the formation of passivation layer 808.

At sub-operation 704, body 602 is formed.

Body 602 is a semi-rigid disc of electrically insulating material that has good mechanical stability and strength in the x-y plane but is substantially compressible in the z-direction. Body 602 is also flexible out of the x-y plane to enable it to conform to slight non-planarity and/or roughness at surfaces 218 and 224.

In the depicted example, body 602 includes compressible layer 608, which is sandwiched between strength layers 610-1 and 610-2. Body 602 is formed by sequential deposition of strength layer 610-1, compressible layer 608, and strength layer 610-2.

Strength layer 610-1 is a layer of Parylene having a thickness of approximately 800 nm. In some embodiments, strength layer 610-1 has a different thickness within the range of approximately 100 nm to approximately 1 micron. Parylene is attractive for use in embodiments of the present invention because it is an electrically insulating material having a relatively high modulus of elasticity (i.e., Young's modulus) but is also flexible out of plane (i.e., out of the x-y plane as shown). Typically, strength layer 610-1 is deposited using conventional chemical vapor deposition (CVD), although other deposition techniques can be used in accordance with the present invention.

Compressible layer 608 is a layer of polydimethylsiloxane (PDMS) having a thickness of approximately 10 microns. In some embodiments, compressible layer 608 has a different thickness within the range of approximately 100 nm to approximately 1 micron. Polydimethylsiloxane (PDMS) is attractive for use in compressible layer because it is an electrically insulating material that can be deposited to have a relatively lower modulus of elasticity. Typically, compressible layer 608 is deposited via a spin-coating process; however other deposition methods are within the scope of the present invention. Due to its relatively low modulus of elasticity, compressible layer 608 is substantially compressible in the z-direction. Unfortunately, its low modulus of elasticity makes it subject to tearing when subjected to tensile stress.

Strength layer 610-2 is analogous to strength layer 610-1. By sandwiching compressible layer 608 with strength layers 610-1 and 610-2, the robustness of body 602 is improved beyond that of only compressible layer 608. In some embodiments, however, body 602 includes only compressible layer 608.

At sub-operation 705, body 602 is patterned to define openings 812, which extend down to regions 808. Openings 812 have a substantially circular cross-section with a diameter of approximately 2 microns. Openings 812 are arranged in a two-dimensional array having a periodicity of approximately 5 microns in each dimension. In some embodiments, openings 812 have a different cross-sectional shape and/or a different cross-sectional dimension. In some embodiments, openings 812 are arranged in a two-dimensional arrangement that is aperiodic in at least one dimension. In some embodiments, openings 812 are arranged in a substantially random two-dimensional arrangement.

Openings 812 function as molds for the deposition of the conductive material that defines conductors 604. Body 602 is patterned by forming a mask layer on surface 220 and etching the layers of body 602 in a directional reactive-ion etch (RIE). Due to the thickness of body 602, it is preferable that the mask layer include a low-residual stress hard mask, such as a metal or germanium layer whose mask pattern is defined using conventional photolithography and dry etching. After formation of openings 812, the hard mask is removed from surface 220.

Figure 8B:
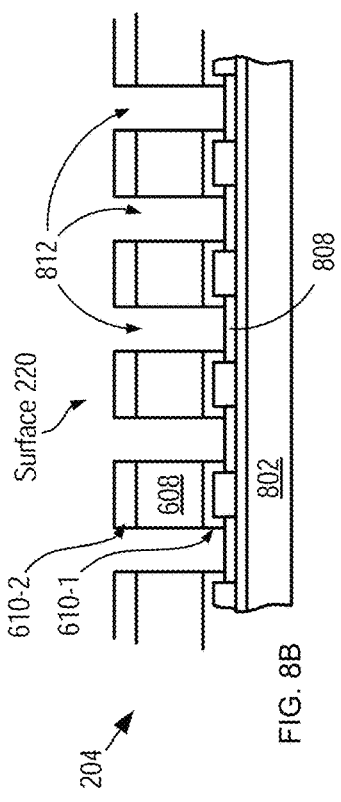

FIG. 8B depicts interposer 204 after the definition of openings 812.

At sub-operation 706, conductors 604 are formed within openings 812.

Conductors 604 are electrically conductive paths formed in openings 812 such that they extend between surfaces 220 and 222. In the depicted example, conductors 604 extend slightly above strength layer 610-2 such that surface 220 is non-planar. Such a configuration advantageously concentrates applied force onto the exposed faces of the conductors when surface 220 is subsequently bonded with surface 218 of wire bundle 202.

Typically, conductors 602 are formed by electroplating copper into openings 812. Electrical contact for the electroplating process is established with each of regions 808 via sacrificial layer 804. Although in the illustrative embodiment conductors 602 comprise copper, it will be clear to one skilled in the art, after reading this Specification, how to specify, make, and use alternative embodiments wherein conductors 602 comprise a different electrically conductive material (e.g., metals, such as palladium, copper, gold, etc.) and/or are formed via a deposition process other than electroplating, such as electroless deposition, sputtering, evaporation, e-beam evaporation, chemical vapor deposition, and the like.

Figure 8C:
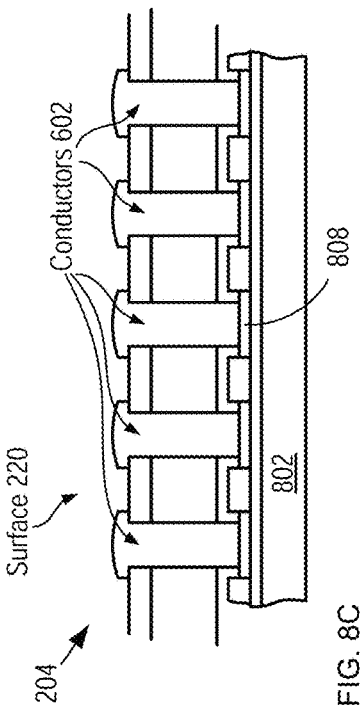

FIG. 8C depicts interposer 204 after the formation of conductors 602.

At sub-operation 707, substrate 802 is removed from interposer 204. Typically, removal of substrate is achieved by selectively etching sacrificial layer 804 away in a suitable sacrificial etch.

Figure 8D:
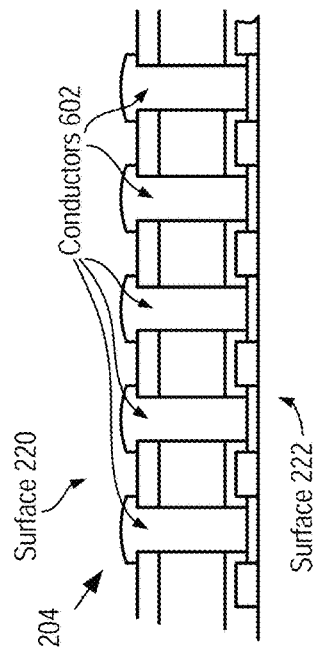

FIG. 8D depicts interposer 204 after the removal of substrate 802.

It will be clear to one skilled in the art, after reading this Specification, that sub-method 700 represents only one of many methods suitable for forming an interposer in accordance with the present invention. Further, one skilled in the art will recognize that the dimensions and materials described above are merely exemplary and myriad alternative dimensions and materials can be used without departing from the scope of the present invention.

For example, in some embodiments, interposer 204 is an electrically insulating membrane that has been track etched to form a plurality of nanometer-scale pores (e.g., 100-nm diameter) that extend through its thickness, where the pores are subsequently filled with an electrically conductive material, such as gold, etc. In such embodiments, exemplary materials suitable for use in body 602 include polyesters (e.g., polycarbonate, etc.), other polymers (e.g., diblock polymers, spun polymers, etc.), and the like. Additional alternative methods for forming interposer 204 include, without limitation, forming nanowire arrays in diblock copolymer templates (as described by Thurn-Albrecht, et al., in *Science*, Vol. 15, pp. 2126-2129, (2000)), coating a nanowire or nanotube array with a layer of polymer via spin-coating, spin-casting, doctor-blading, etc., and the like.

Further, although the illustrative embodiment comprises an interposer that is formed as a stand-alone unit, it will be clear to one skilled in the art, after reading this Specification, how to specify, make, and use alternative embodiments of the present invention wherein an interposer is formed in integrated fashion directly on IC 206 or on surface 218 of wire bundle 202.

For example, an interposer can be integrated with IC 206 by disposing a compressive layer on surface 224 and patterning the compressive layer to define a plurality of openings (analogous to openings 812 described above) that extend to surface 224. These openings can be either aligned with bond pads 226 or, preferably, arranged in a high-density arrangement having an inter-opening spacing that is smaller than at least one lateral dimension of the bond pads. The openings are then filled with electrically conductive material to give rise to conductors that are electrically connected to the bond pads. In some cases, the current-providing capability of the circuitry of IC 206 can be used to enable electrochemical deposition of the conductive material selectively in those openings aligned with bond pads.

FIGS. 9A-B depict scanning-electron microscope (SEM) pictures, at different magnifications, of a region of interposer 204.

FIG. 9C depicts a conductivity map of interposer 204.

Returning now to method 300, at operation 304, interposer 204 and wire bundle 202 are joined by placing surfaces 218 and 220 into physical contact. This establishes electrical connectivity between each of wires 206 and at least one conductor 604. In some embodiments, the joining of interposer 204 and bundle 202 is facilitated by mounting the bundle in a fixture that can impart vertical force at surfaces 218 and 220, but that also has some rotational compliance about the x- and y-axes to facilitate planar, conformal contact between these surfaces.

At operation 305, interposer 204 and IC 206 are joined by placing surface 222 and bond pads 226 into physical contact.

It should be noted that operations 304 and 305 give rise to electrical connectivity between wires 206 and bond pads 226 through the conductors of interposer 204. The compressibility of the interposer enables the electrical connections to be established via conductors 602 without the conductors deforming plastically (i.e., the conductors remain elastically deformable elements). As a result, this compressibility enables slight corrections in rotation about the x- and y-axes as the surfaces are brought into contact.

At optional operation 306, a compressive force is applied between wire bundle 202 and IC 206 to enhance the electrical connectivity between wires 208 and bond pads 226 via conductors 602.

In some embodiments, a metallurgical or chemical bond (e.g., a eutectic bond, oxygen-assisted plasma bond, etc.) is established between wires 208 and conductors 602 and/or between conductors 602 and bond pads 226.

It is an aspect of the present invention that the use of an interposer having a pattern of very fine conductors whose spacing is smaller than the pitch of the bond pads of IC 206 mitigates, or avoids altogether, the need for fine alignment between coupling bundle 202 and IC 206 when electrically connective them via the interposer. It should be noted that this benefit accrues even for embodiments wherein the pattern of conductors in the interposer is random. It is preferable, however, that the spatial distribution of conductors is substantially even. The ease of aligning these elements arises from the fact that the fine conductors are electrically isolated from one another laterally within the interposer, while simultaneously providing excellent electrical conductivity through the interposer's thickness. Those conductors that happen to be between bond pads and/or bundle wires simply remain electrically unconnected while electrical connectivity is provided by those fine conductors that are within the boundaries of the bond pads and wires. Embodiments of the present invention, therefore, are afforded advantages over the prior art.

FIG. 10 depicts an overlap showing outlines of bond pads of IC 206 overlaid on the surface of interposer 204. Image 1000 evinces that each of bond pads 226-1 and 226-2 contacts multiple conductors 604 without interference from neighboring bond pad. In other words, each bond pad is contacted, but there is no shorting between bond pads.

It should be noted that bundle 202 is modular. As a result many IC chips could be used in parallel. In some embodiments, the present invention also directly enables brain-machine interfaces that can read out brain activity at a real data rate of ~1 kHz times the bundle size. This would mean that a bundle of 480 k wires would have the capability of interfacing with neuroprosthetics at a data rate equivalent to USB 2.0. Such a capability represents a qualitative change the treatment options for paralysis.

Figure 11:
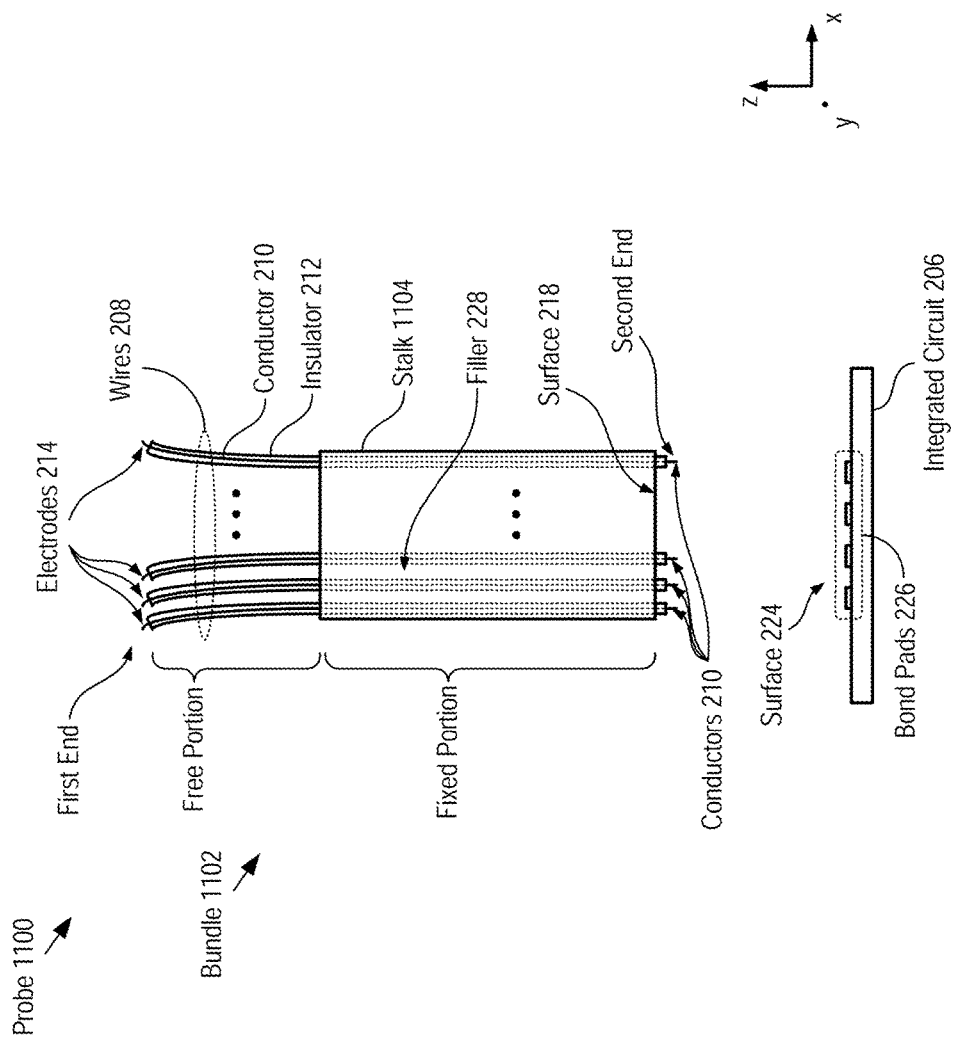
FIG. 11 depicts a schematic drawing of a probe in accordance with a first alternative embodiment of the present invention.

FIG. 11 depicts a schematic drawing of a probe in accordance with a first alternative embodiment of the present invention. Probe 1100 includes wire bundle 1102 and IC 206. Wire bundle 1102 is analogous to wire bundle 202; however, surface 218 of stalk 1104 is relieved slightly such that the second end of each of conductors 210 projects from surface 218 toward surface 224 of IC 206.

Typically, the relief of surface 218 is done in a two-step process. First, filler 228 is first etched back using an appropriate etch (e.g., an oxygen plasma, or wet-chemical etch) to expose the fixed ends of wires 208. Second, insulator 212 is optionally etched back to expose a portion of each conductor 210. The amount of each conductor 210 that is exposed is preferably very small (analogous to a conventional bond pad at surface 218). As a result, for the purposes of this Specification, including the appended claims, the second end of each wire 208, although projecting slightly from stalk 1104, is still defined as terminating at surface 218. It should be noted that, by projecting beyond surface 218, the second ends of wires 208 collectively define a structure that operates as an interposer integrated directly on wire bundle 1102.

By virtue of the exposed portions of conductors 210, wire bundle 1102 can be mounted directly to IC 206 (i.e., without interposer 204) by mating surfaces 218 and 224. In some embodiments, however, interposer 204 is used to couple wire bundle 1102 and IC 206 to further assure good electrical contact between wires 208 and bond pads 226.

Preferably, the electrical connectivity between wires 206 and bond pads 226 is established during the alignment of surfaces 218 and 224 using a compressive force that is limited such that conductors 210 do not deform plastically during this alignment procedure. In other words, the electrical connections are established via elastically deformable elements (i.e., deformable elements that retain their elasticity) that enable slight corrections in rotation about the x- and y-axes as the surfaces are brought into contact.

As discussed above and with respect to FIG. 2, it is preferable that the inter-wire spacing within wire bundle 1102 is different than the pitch of bond pads 226. Additional relaxation of alignment consideration during the assembly of probe 1100 can be achieved by arranging wires 208 within bundle 1102 such that they are spaced by a distance smaller than at least one lateral dimension of bond pads 226.

It should be noted that probes in accordance with the present invention enable improved deep-brain recording as well as stimulation. As mentioned above, the ability to provide deep-brain stimulation enables treatment options that are simply not possible with prior-art probes. One skilled in the art will recognize that the effectiveness of DBS treatment depends strongly on stimulation parameters. Because prior-art DBS electrodes provide only a few leads for stimulation, they enable only two stimulation parameters to be adjusted to fit patients' needs: frequency (100-130 Hz) and intensity (0.5-2V).

Figures 12A, 12B:
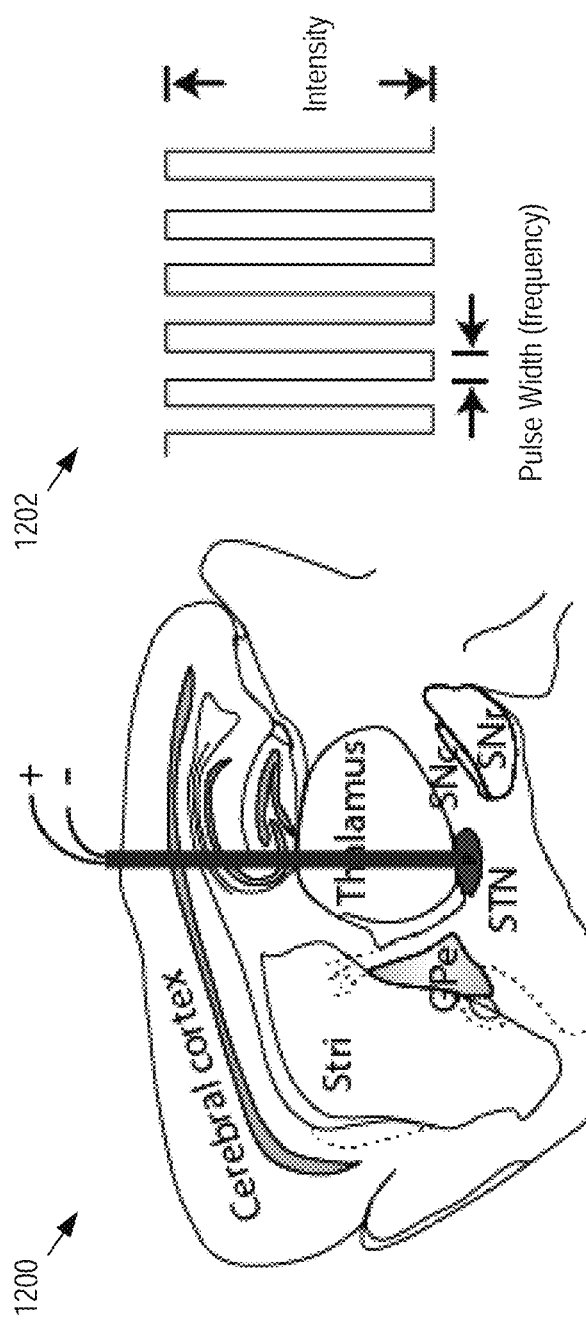
FIGS. 12A-B depict a schematic drawing of a prior-art deep-brain stimulation approach and prior-art deep-brain stimulation protocol, respectively.

FIGS. 12A-B depict a schematic drawing of a prior-art deep-brain stimulation approach and prior-art deep-brain stimulation protocol, respectively.

In contrast, deep-brain probes in accordance with the present invention have hundreds to thousands of leads, where each pair can be used for stimulation.

FIG. 13 depicts operations of a method for interfacing with a brain in accordance with the illustrative embodiment of the present invention. Method 1300 begins with operation 1301, wherein a desired response of a test subject is established. Method 1300 is described with continuing reference to FIG. 2, as well as reference to FIG. 14.

At operation 1302, probe 200 is inserted into the deep-tissue regions of the brain of test subject 1402. During insertion of probe 200, the free ends of wires 208 splay out within the brain tissue such that electrodes 214 deploy in a three-dimensional arrangement.

FIG. 14A depicts a two-dimensional cross-section of a three-dimensional electrode pattern that manifests in the brain of a test subject. Electrode pattern 1400 is a two-dimensional cross-section of the three-dimensional distribution of electrodes 214 as arranged within the brain of test subject 1402. Pattern 1400 includes a plurality of electrode pairs, across each of which a stimulus signal can be applied by providing appropriate voltage levels, frequencies, and relative timing at their corresponding bond pads 226.

At operation 1303, for i=1 through M, two-dimensional voltage spatial pattern pattern-i is generated at bond pads 226.

FIG. 14B depicts four examples of stimulation patterns attainable with a probe in accordance with the present invention. Compared to conventional probes, which can only target small numbers of neurons and passing axons at its implant site, probe 200 enables coverage of a large area in the target subthalamic nucleus. Because of the small size of each individual electrode, both subthalamic-nucleus neurons themselves and the passing corticofugal axons can be effectively activated. This enables stimulation protocols that can be stored as two-dimensional barcodes for personalized treatment that is uniquely designed and tested for individual subject patients.

At operation 1304, a subject response, response-i, of test subject 1402 to pattern-i is determined. In some embodiments, at least one of the intensity, frequency and relative timing for the output signal at each stimulation lead is fine-tuned to achieve a desired subject stimulation via the applied voltage spatial pattern.

At operation 1305, a preferred voltage spatial pattern is selected based on voltage spatial patterns pattern-1 through pattern-M and the desired subject response established in operation 1301.

Probes in accordance with the present invention enable the use of patterned stimulation using bundles of >1,000 individually addressable electrodes for deep-brain stimulation in a mouse model of Parkinson's disease.

FIGS. 14C-D depict examples of tests for motor behavior of a mouse model as enabled by the present invention. Probes in accordance with the present invention enable testing of variable patterns of activity in relieving motor symptoms in mouse model of Parkinson's disease (PD), including various motor behaviors, such as cylinder test for limb use asymmetry (FIG. 14C) and open field test for activity before, during and after deep-brain stimulation (FIG. 14D).

It is to be understood that the disclosure teaches just one example of the illustrative embodiment and that many variations of the invention can easily be devised by those skilled in the art after reading this disclosure and that the scope of the present invention is to be determined by the following claims.

What is claimed is:

1. A deep-brain probe comprising:
   (A) a wire bundle comprising a first plurality of wires that are arranged in a first two-dimensional arrangement, wherein each of the first plurality of wires has a first end and a second end, and wherein each of the first plurality of wires includes:
      a core that is electrically conductive;
      an electrical insulator that surrounds the core along the length of the wire; and
      an electrode that is electrical-insulator-free;
   wherein the wire bundle has a first portion in which the first plurality of wires is mechanically joined together to collectively define a stalk, the first end of each wire of the plurality thereof terminating at a first surface of the stalk; and
   wherein the wire bundle has a second portion in which each wire of the first plurality thereof is unrestrained, the second end and the electrode of each wire of the plurality thereof being in the second portion;
   (B) a first integrated circuit comprising a plurality of bond pads that is arranged in a second two-dimensional arrangement; and
   (C) an interposer that includes:
      (i) a body having a first surface and a second surface, the body comprising a first material that is an electrical insulator, and the body being compressible, wherein the body includes:
         (a) a first layer comprising the first material, the first material being characterized by a first modulus of elasticity;
         (b) a second layer that includes the first surface; and
         (c) a third layer that includes the second surface, the second and third layers comprising a third material having a second modulus of elasticity that is higher than the first modulus of elasticity;
         wherein the first layer is between the second and third layers; and
      (ii) a plurality of conductors that extend through the body from the first surface to the second surface, wherein each of the plurality of conductors comprises a second material that is electrically conductive;
   wherein the wire bundle, first integrated circuit, and interposer are arranged such that each of the plurality of bond pads is electrically connected with each of one or more wires of the first plurality thereof via at least one of the plurality of conductors.

2. The probe of claim 1 wherein a first bond pad of the plurality of bond pads is electrically connected to a second plurality of wires via a second plurality of conductors, and wherein a second bond pad of the plurality of bond pads is electrically connected to a third plurality of wires via a third plurality of conductors, the second plurality of wires and third plurality of wires being mutually exclusive, the first plurality of wires including the second plurality of wires and the third plurality of wires, and the first plurality of conductors including the second plurality of conductors and the third plurality of conductors.

3. The probe of claim 1 wherein the second two-dimensional arrangement is characterized by an inter-bond-pad spacing in a first dimension, and wherein the first two-dimensional arrangement is characterized by a first inter-wire spacing in the first dimension that is different than the inter-bond-pad spacing.

4. The probe of claim 1 wherein each of the plurality of bond pads has a first width in a first dimension of the second two-dimensional arrangement, and wherein the plurality of conductors is arranged such that it is characterized by a first spacing in the first dimension that is smaller than the first width.

5. The probe of claim 1 wherein the first integrated circuit is operative for generating a plurality of two-dimensional spatial patterns of voltages on the plurality of bond pads.

6. The probe of claim 1 wherein the electrode of a first wire of the plurality thereof comprises a first material having a first electrical impedance and a first coating comprising a second material that has a second electrical impedance, the second electrical impedance being lower than the first electrical impedance.

7. A deep-brain probe comprising:
   a wire bundle comprising a first plurality of wires, each wire including:
      a core that is electrically conductive, the core having an end face;
      an electrical insulator that surrounds the core along the length of the wire; and
      an electrode that is electrical-insulator-free;
      wherein the plurality of end faces are arranged in a first two-dimensional arrangement at a first surface;
   a first integrated circuit comprising a first plurality of bond pads that is arranged in a second two-dimensional arrangement at a second surface; and
   an interposer including:
      a body having a third surface and a fourth surface, the body comprising a material that is substantially electrically insulating and compressible;
      a first plurality of conductors that extend from the third surface to the fourth surface;
   wherein the first surface and third surface are in physical contact such that each end face of the plurality thereof is in physical contact and electrically connected with at least one conductor of the first plurality thereof and no conductor of the first plurality thereof is directly electrically connected with more than one end face; and
   wherein the second surface and the fourth surface are in physical contact such that each bond pad of the first plurality thereof is directly electrically connected with at least one conductor of the first plurality thereof and no conductor is directly electrically connected with more than one bond pad of the first plurality thereof.

8. The deep-brain probe of claim 7 wherein the first two-dimensional arrangement is different than the second two-dimensional arrangement.

9. The probe of claim 7 wherein the body includes:
   a first layer comprising the first material, the first material being characterized by a first modulus of elasticity;

a second layer that includes the first surface; and a third layer that includes the second surface, the second and third layers comprising a third material having a second modulus of elasticity that is higher than the first modulus of elasticity;

wherein the first layer is between the second and third layers.

10. The probe of claim 7 wherein a first bond pad of the first plurality of bond pads is electrically connected to a second plurality of wires via a second plurality of conductors, and wherein a second bond pad of the first plurality of bond pads is electrically connected to a third plurality of wires via a third plurality of conductors, the second plurality of wires and third plurality of wires being mutually exclusive, the first plurality of wires including the second plurality of wires and the third plurality of wires, and the first plurality of conductors including the second plurality of conductors and the third plurality of conductors.

11. The probe of claim 7 wherein the first integrated circuit is operative for generating a plurality of two-dimensional spatial patterns of voltages on the first plurality of bond pads.

12. The probe of claim 7 wherein the wire bundle has a first portion in which the first plurality of wires is mechanically joined together to collectively define a stalk that includes the first surface, and wherein the wire bundle has a second portion in which each wire of the first plurality thereof is unrestrained, the electrode of each wire of the plurality thereof being in the second portion.

13. The probe of claim 7 wherein the electrode of a first wire of the plurality thereof comprises a first material having a first electrical impedance and a first coating comprising a second material that has a second electrical impedance, the second electrical impedance being lower than the first electrical impedance.

14. A deep-brain probe comprising:

a wire bundle comprising a first plurality of wires, each wire including:
  a core that is electrically conductive, the core having an end face;
  an electrical insulator that surrounds the core along the length of the wire; and
  an electrode that is electrical-insulator-free;
  wherein the plurality of end faces are arranged in a first two-dimensional arrangement at a first surface;

a first integrated circuit comprising a first plurality of bond pads that is arranged in a second two-dimensional arrangement at a second surface, wherein the first integrated circuit is operative for generating a plurality of two-dimensional spatial patterns of voltages on the first plurality of bond pads; and an interposer including a first plurality of conductors that extend from a third surface of a body to a fourth surface of the body such that the interpose is conductive along a first direction from the third surface to the fourth surface and substantially electrically insulating along a second direction that is orthogonal with the first direction;

wherein the first surface and third surface are in physical contact such that each end face of the plurality thereof is in physical contact and electrically connected with at least one conductor of the first plurality thereof;

wherein the second surface and the fourth surface are in physical contact such that each bond pad of the first plurality thereof is directly electrically connected with at least one conductor of the first plurality thereof; and wherein the second two-dimensional arrangement has an average inter-bond-pad spacing along the second direction and the first plurality of conductors has an average inter-conductor spacing along the second direction, and wherein the average inter-conductor spacing is smaller than the average inter-bond-pad spacing.

15. The probe of claim 14 wherein the first two-dimensional arrangement has an average inter-wire spacing along the second direction, and wherein the average inter-conductor spacing is smaller than the average inter-wire spacing.

16. The probe of claim 15 wherein the second two-dimensional arrangement has an average inter-bond-pad spacing along the second direction, and wherein the average inter-conductor spacing is smaller than the average inter-bond-pad spacing.

17. The probe of claim 14 wherein the wire bundle has a first portion in which the first plurality of wires is mechanically joined together to collectively define a stalk that includes the first surface, and wherein the wire bundle has a second portion in which each wire of the first plurality thereof is unrestrained, the electrode of each wire of the plurality thereof being in the second portion.

18. The probe of claim 14 wherein the electrode of a first wire of the plurality thereof comprises a first material having a first electrical impedance and a first coating comprising a second material that has a second electrical impedance, the second electrical impedance being lower than the first electrical impedance.

* * * * *